(12) United States Patent
Mcminn

(10) Patent No.: US 8,177,852 B2
(45) Date of Patent: May 15, 2012

(54) HIP JOINT PROSTHESIS

(75) Inventor: Derek James Wallace Mcminn, Stourbridge (GB)

(73) Assignee: Smith & Nephew, Inc. (GB)

(*) Notice: Subject to any disclaimer, the term of this patent is extended or adjusted under 35 U.S.C. 154(b) by 0 days.

(21) Appl. No.: 12/889,541

(22) Filed: Sep. 24, 2010

(65) Prior Publication Data

US 2011/0015755 A1    Jan. 20, 2011

Related U.S. Application Data

(62) Division of application No. 10/396,616, filed on Mar. 25, 2003, now Pat. No. 7,879,106.

(30) Foreign Application Priority Data

Mar. 26, 2002  (GB) .................................. 0207170.2

(51) Int. Cl.
*A61F 2/32* (2006.01)
(52) U.S. Cl. ................................... 623/22.44
(58) Field of Classification Search ............... 623/22.11, 623/22.4–23.15, 23.39–23.45, 20.35–20.36, 623/22.15; 606/79–89, 99
See application file for complete search history.

(56) References Cited

U.S. PATENT DOCUMENTS

| | | | | |
|---|---|---|---|---|
| 2,685,877 A | * | 8/1954 | Dobelle ..................... | 623/23.11 |
| 2,718,228 A | * | 9/1955 | Van Steenbrugghe ..... | 623/23.14 |
| 2,781,758 A | | 2/1957 | Chevalier | |
| 2,934,065 A | * | 4/1960 | Townley .................... | 623/23.14 |
| 3,064,645 A | | 11/1962 | Ficat et al. | |
| 3,521,302 A | | 7/1970 | Muller | |
| 3,744,061 A | | 7/1973 | Frost | |
| 3,848,273 A | * | 11/1974 | Frey ........................... | 623/23.29 |
| 3,874,003 A | | 4/1975 | Moser et al. | |
| 3,987,499 A | | 10/1976 | Scharbach et al. | |
| 4,005,495 A | * | 2/1977 | Locke et al. ............... | 623/23.14 |
| 4,032,994 A | | 7/1977 | Frey | |
| 4,123,806 A | * | 11/1978 | Amstutz et al. ........... | 623/22.39 |
| 4,224,699 A | * | 9/1980 | Weber ........................ | 623/23.14 |
| 4,279,042 A | * | 7/1981 | Andriacchi et al. ....... | 623/23.15 |
| 4,332,036 A | | 6/1982 | Sutter et al. | |
| 4,359,785 A | | 11/1982 | Niederer | |
| 4,608,055 A | * | 8/1986 | Morrey et al. ............. | 623/22.46 |
| 4,658,808 A | | 4/1987 | Link | |
| 4,738,681 A | | 4/1988 | Koeneman et al. | |

(Continued)

FOREIGN PATENT DOCUMENTS

CH            676922         3/1991
(Continued)

OTHER PUBLICATIONS

Huggler, "A new Approach Towards Hip-Prosthesis Design"; Arch Orthop Traumat Surg; 1980, vol. 97, pp. 141-144.

(Continued)

*Primary Examiner* — Alvin J Stewart
(74) *Attorney, Agent, or Firm* — Fulbright & Jaworski, L.L.P.

(57) ABSTRACT

A femoral implant for fitting to a resected femur comprises a section having a frustoconical external form, a stem part extending away from the section to a distal end of the implant, and a femoral head extending directly away from the section to the proximal end of the implant. The implant could have the femoral head integral with the section, or as a separate component secured thereto, with the stem being a separate one piece component incorporating the section.

19 Claims, 5 Drawing Sheets

U.S. PATENT DOCUMENTS

Figure 1:
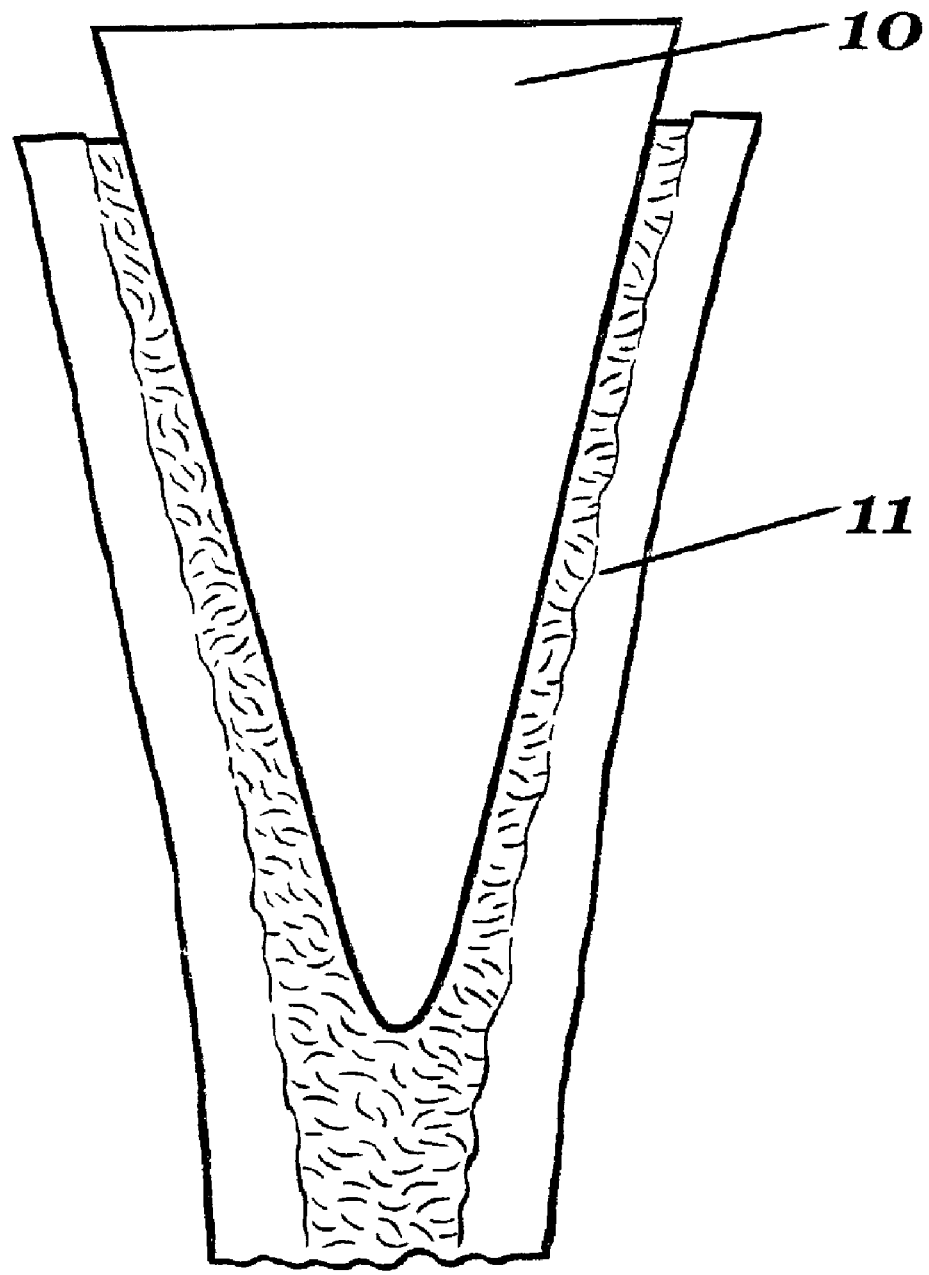

| | | | |
|---|---|---|---|
| 4,752,296 A * | 6/1988 | Buechel et al. | 623/23.14 |
| 4,840,632 A | 6/1989 | Kampner | |
| 4,846,841 A | 7/1989 | Oh | |
| 4,938,771 A | 7/1990 | Vecsei et al. | |
| 4,950,300 A | 8/1990 | Langlais | |
| 4,976,740 A | 12/1990 | Kleiner | |
| 4,990,161 A * | 2/1991 | Kampner | 623/18.11 |
| 5,133,764 A * | 7/1992 | Pappas et al. | 623/23.14 |
| 5,222,985 A | 6/1993 | Homsy | |
| 5,263,991 A | 11/1993 | Wiley et al. | |
| 5,310,408 A | 5/1994 | Schryver et al. | |
| 5,376,120 A | 12/1994 | Sarver et al. | |
| 5,389,107 A * | 2/1995 | Nassar et al. | 623/23.17 |
| 5,458,653 A * | 10/1995 | Davidson | 623/23.36 |
| 5,571,193 A | 11/1996 | Kampner | |
| 5,641,323 A | 6/1997 | Caldarise | |
| 5,658,352 A * | 8/1997 | Draenert | 623/22.4 |
| 5,733,338 A | 3/1998 | Kampner | |
| 5,735,905 A | 4/1998 | Parr | |
| 5,800,553 A | 9/1998 | Albrektsson et al. | |
| 5,800,560 A * | 9/1998 | Draenert | 623/22.43 |
| 5,871,547 A | 2/1999 | Abouaf et al. | |
| 5,871,549 A * | 2/1999 | Jayashankar et al. | 623/22.4 |
| 6,013,104 A | 1/2000 | Kampner | |
| 6,033,439 A | 3/2000 | Camino et al. | |
| 6,059,830 A | 5/2000 | Lippincott, III et al. | |
| 6,096,084 A * | 8/2000 | Townley | 623/23.12 |
| 6,120,542 A | 9/2000 | Camino et al. | |
| 6,120,544 A * | 9/2000 | Grundei et al. | 623/23.14 |
| 6,156,069 A | 12/2000 | Amstutz | |
| 6,224,634 B1 * | 5/2001 | Keller | 623/23.11 |
| 6,284,002 B1 * | 9/2001 | Sotereanos | 623/27 |
| 6,368,352 B1 | 4/2002 | Camino et al. | |
| RE37,964 E * | 1/2003 | Prats et al. | 623/23.11 |
| 7,238,208 B2 * | 7/2007 | Camino et al. | 623/19.12 |
| 7,494,509 B1 * | 2/2009 | Hershberger et al. | 623/23.35 |
| 7,641,699 B2 * | 1/2010 | Unger | 623/23.35 |
| 7,879,106 B2 * | 2/2011 | McMinn | 623/22.44 |
| 2002/0072805 A1 | 6/2002 | Sullivan et al. | |
| 2002/0095215 A1 * | 7/2002 | Camino et al. | 623/19.14 |
| 2002/0128720 A1 * | 9/2002 | Masini | 623/22.42 |
| 2002/0133234 A1 * | 9/2002 | Sotereanos | 623/23.26 |
| 2003/0014123 A1 * | 1/2003 | Copf et al. | 623/23.14 |
| 2003/0163202 A1 * | 8/2003 | Lakin | 623/22.15 |
| 2004/0024468 A1 * | 2/2004 | Lualdi et al. | 623/22.45 |
| 2005/0256585 A1 * | 11/2005 | Park et al. | 623/23.14 |
| 2008/0200990 A1 * | 8/2008 | McTighe et al. | 623/22.42 |
| 2009/0088863 A1 * | 4/2009 | Boucher et al. | 623/22.4 |
| 2010/0100193 A1 * | 4/2010 | White | 623/22.43 |
| 2011/0166666 A1 * | 7/2011 | Meulink et al. | 623/22.42 |

FOREIGN PATENT DOCUMENTS

| | | |
|---|---|---|
| DE | 923383 | 7/1954 |
| DE | 3023354 | 4/1981 |
| DE | 19904126 | 3/1999 |
| EP | 0025835 | 4/1981 |
| EP | 0176711 | 4/1986 |
| EP | 0228523 | 7/1987 |
| EP | 0302850 | 2/1989 |
| EP | 0477113 | 3/1992 |
| EP | 0579868 | 1/1994 |
| EP | 0666069 | 8/1995 |
| EP | 0711534 | 5/1996 |
| EP | 1138283 | 10/2001 |
| EP | 1332736 | 4/2005 |
| FR | 2021313 | 7/1970 |
| FR | 2134170 | 12/1972 |
| FR | 2363837 | 3/1978 |
| FR | 2429010 | 1/1980 |
| FR | 2629707 | 10/1989 |
| FR | 2644690 | 9/1990 |
| FR | 2706283 | 12/1994 |
| GB | 2069340 | 8/1981 |
| GB | 2139097 | 11/1987 |
| GB | 2366733 | 3/2002 |
| JP | 61-094650 | 5/1986 |
| JP | 07-506739 | 7/1995 |
| JP | 09508816 | 9/1997 |
| WO | WO-8911837 | 12/1989 |
| WO | WO-9317639 | 9/1993 |
| WO | WO-9515129 | 6/1995 |
| WO | WO-9716137 | 5/1997 |
| WO | WO-98/07393 | 2/1998 |

OTHER PUBLICATIONS

Office Action dated Nov. 7, 2007 in corresponding U.S. Appl. No. 10/559,950.

Office Action dated Jul. 17, 2008 in corresponding U.S. Appl. No. 10/559,950.

Office Action dated May 21, 2009 in corresponding U.S. Appl. No. 10/559,950.

Office Action dated Sep. 25, 2009 in corresponding U.S. Appl. No. 10/559,950.

* cited by examiner

HIP JOINT PROSTHESIS

Cross-Reference to Related Applications

The present application is a Divisional Application of U.S. application Ser. No. 10/396,616, which was filed on Mar. 25, 2003, entitled HIP JOINT PROSTHESIS and claims priority to Great Britain Application No. 0207170.2, which was filed on Mar. 26, 2002, entitled HIP JOINT PROSTHESIS, the disclosures of which are incorporated by reference herein in their entirety.

This invention relates generally to a hip joint prosthesis, and in particular to a method of fitting a femoral implant to a resected femur, and to the femoral implant per se.

Figure 2:
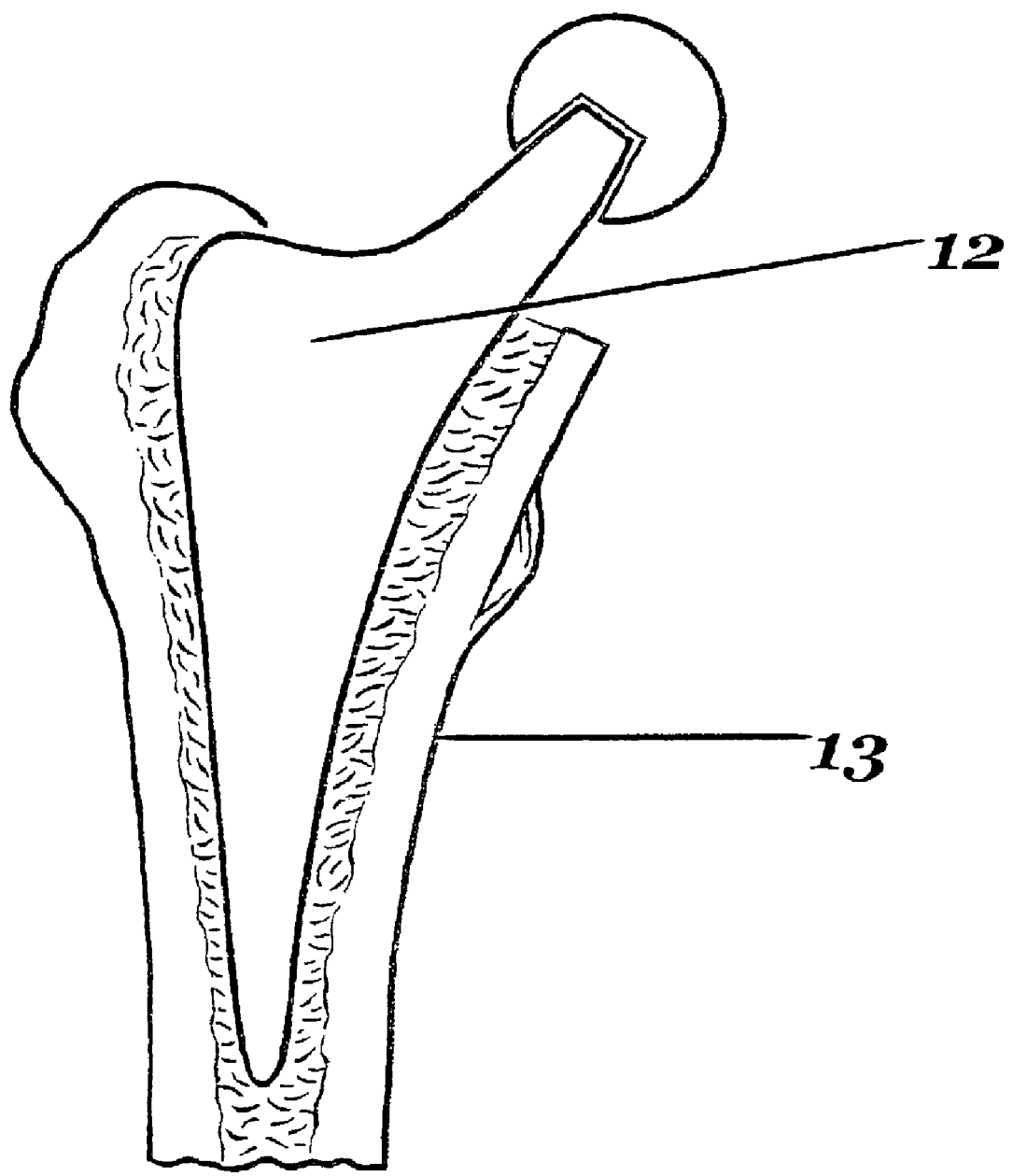

Hip replacements involve the use of an implant stem which is fitted into the medullary canal of the femur. Generally such stems achieve optimum fixation when a tapered prosthesis 10 is fitted in the medullary canal of a tapering bone 11, as schematically shown in FIG. 1. This requirement is generally achieved with a conventional type total hip replacement stem 12 fitted into the proximal femoral portion 13 as shown in FIG. 2.

This form of treatment, however, suffers from the following disadvantages:
1) It requires extensive bone resection of the femoral head and part of the femoral neck.
2) It leads to loading of the shaft of the femur in a non-physiological fashion, leading to distal load transfer and proximal femoral shaft stress shielding.
3) There can be loosening of the total hip replacement stem, as there is a cantilever effect with the point of loading on the prosthetic femoral head at a distance from the point of fixation in the proximal femoral shaft.

With young active patients it is now regular practice to insert a more conservative type of hip replacement known as a resurfacing, and this type of prosthesis overcomes in major part the three disadvantages listed above. However some patients are not suitable for hip resurfacing, mainly on account of poor bone in the zenith of the femoral head due to cystic destruction, as shown at 14 in FIG. 3. With young patients with such cystic destruction, there is a need for a more conservative type of hip replacement than the standard variety shown in FIG. 2.

An example of a more conservative hip replacement is disclosed in EP 0579868 A2. This type of implant attempts to conserve bone, load the femur more proximally and, by retaining most of the patient's femoral neck, resist torsional loading more satisfactorily than the standard total hip replacement. However this type of prosthesis does not fulfil the requirements referred to in relation to FIG. 1. In particular it can be seen from EP 0579868 A2 that the bone in the femoral neck expands into a widened bone in the proximal femoral shaft (inter-trochanteric region), thus not fulfilling the FIG. 1 requirements.

An object of the invention is to provide an improved method of fitting a femoral implant to a resected femur and also an improved femoral implant itself and an improved femoral implant stem.

According to a first aspect of the invention there is provided a method of fitting a femoral implant to a resected femur comprising resecting the femoral bone through the femoral head, machining said resected proximal end of the femur to form a frustoconical or generally frustoconical cavity in the bone, and inserting into said cavity a femoral implant, which in use extends into the medullary canal of the femur.

Preferably the femoral bone is resected through the base of the femoral head. Conveniently the cavity machined into the bone of the femur is symmetrical about a centre line thereof. Advantageously at or adjacent its proximal end the femoral implant is formed with a part having an external surface complementary to the surface of said cavity in the femoral bone. Conveniently a curved stem part of the implant extends away from said part of the implant, and is received in said medullary canal. Said stem part could however be straight.

According to a further aspect of the invention, a femoral implant comprises adjacent a proximal end thereof a section having an external surface of frustoconical or generally frustoconical form, a stem part extending away from said section to a distal end of the implant and a femoral head extending directly away from said section to the proximal end of the implant.

Preferably the femoral head is integral with said section. Advantageously the femoral head is separate from said section. Conveniently the separate femoral head is secured to said section by respective interfitting parts thereof. Desirably a frustoconical spigot extending from said section is received in a complementarily shaped cavity in the femoral head. More preferably the spigot is a tight frictional fit in said cavity, or is cemented therein. The central part of the femoral head is preferably hollow. Desirably the implant is manufactured of cobalt chrome. The stem part is preferably curved, but could be straight.

According to a still further aspect of the invention a stem of a femoral implant has a stem part extending to a distal end of the stem and a section from which the stem part extends, said section having an external surface which is of frustoconical or generally frustoconical form and which terminates at a free end of the section.

Conveniently a spigot extends from said free end of the section for connection, in use, of a femoral head to said stem. Preferably said spigot has a frustoconical external surface. Desirably the stem part is cemented in place or modified for suitable biological fixation, in use. The stem part is preferably curved, but could alternatively be straight.

Figure 3:
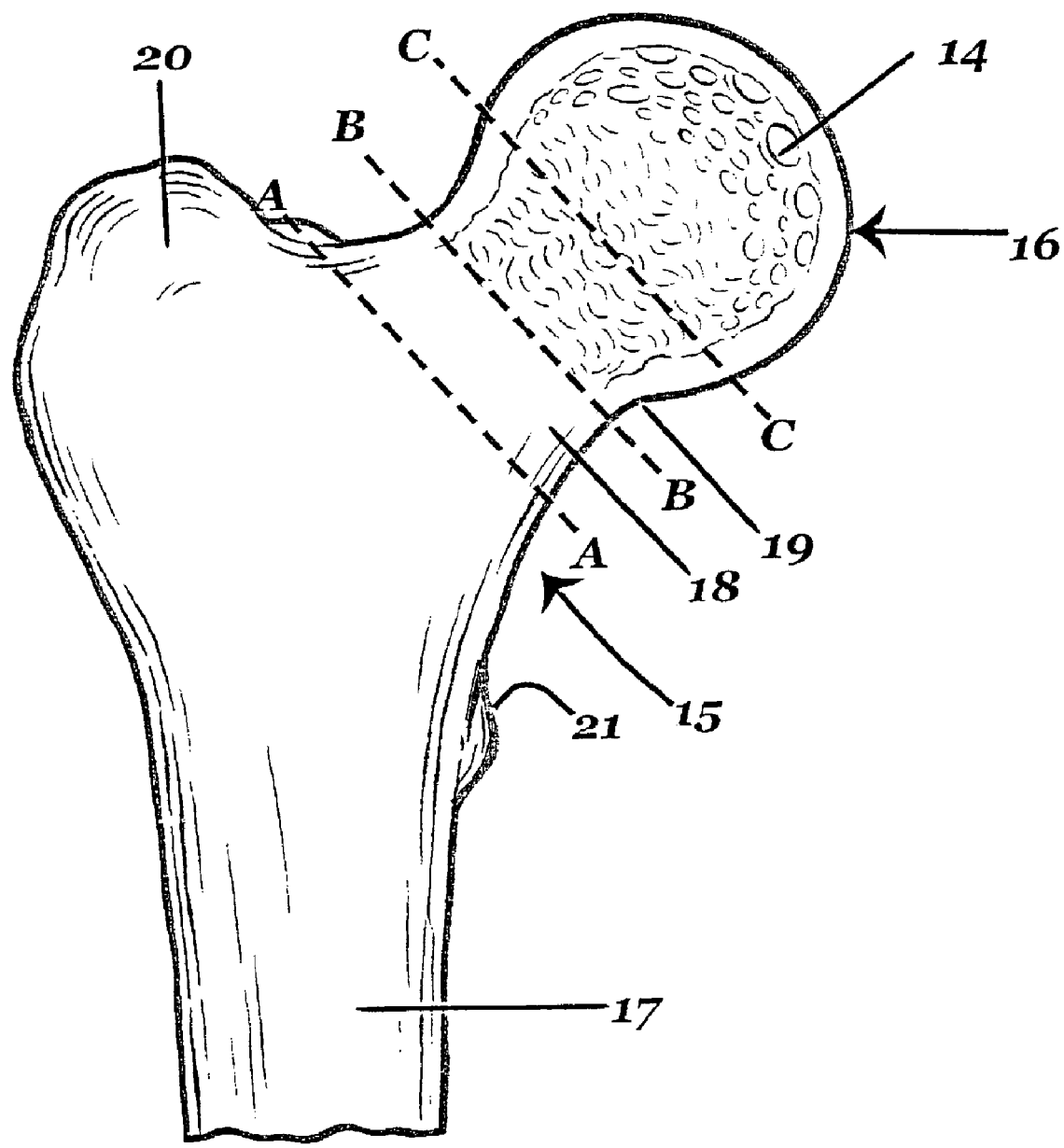
Figure 4:
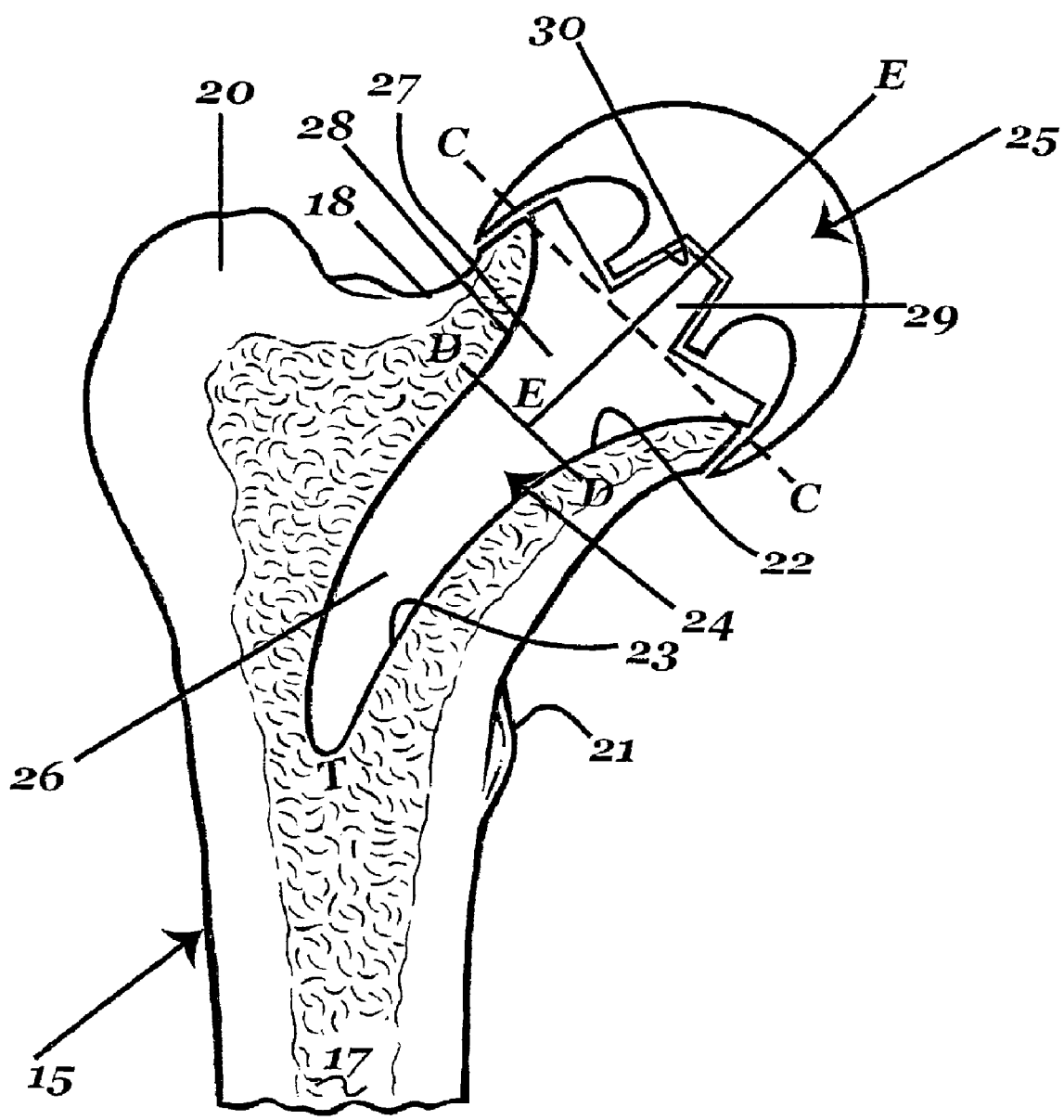
Figure 5:
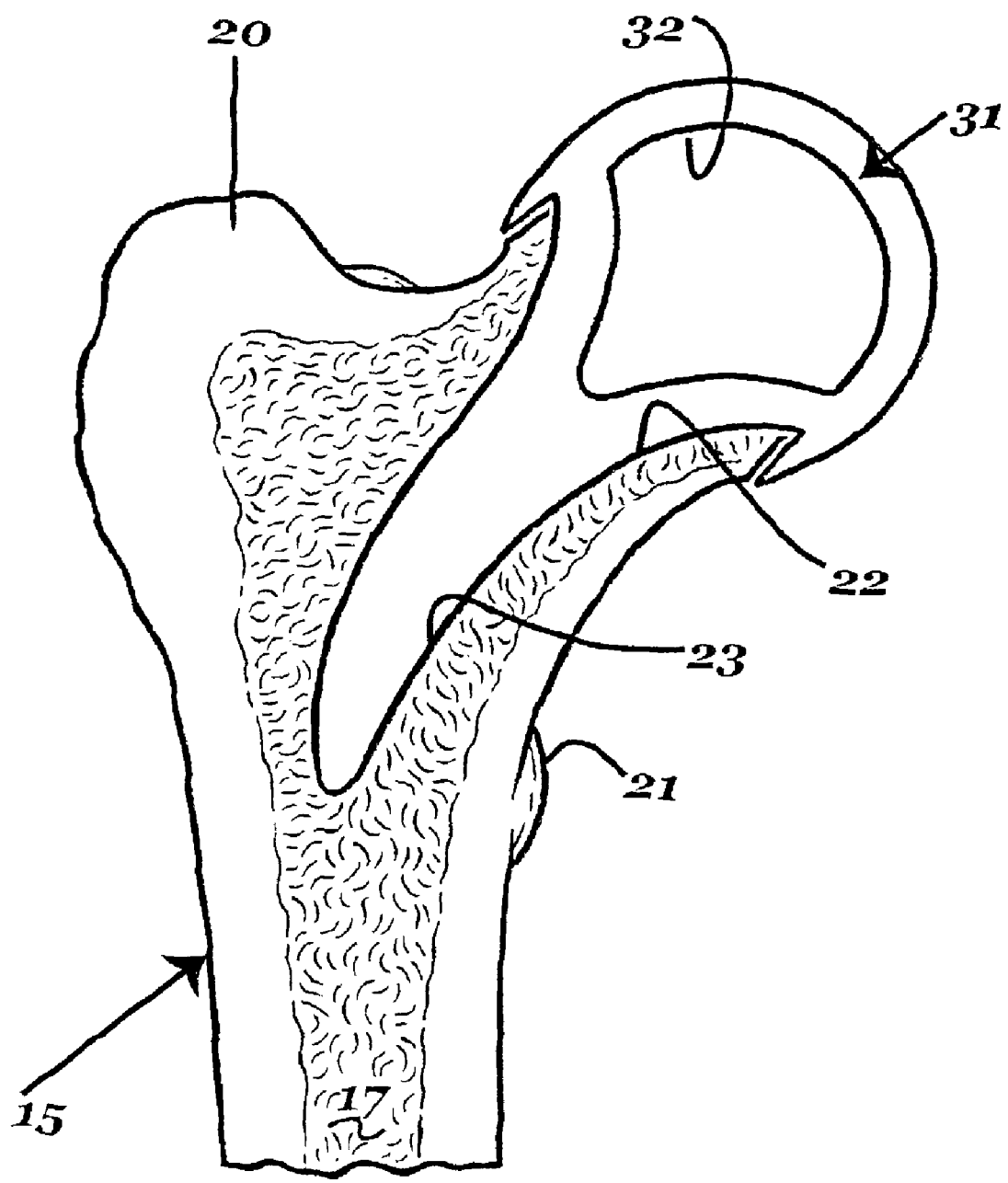

The invention will now be described, by way of example, with reference to the accompanying drawings, in which:

FIG. 1 is a schematic view of an optimum fixation arrangement of a femoral prosthesis, FIG. 2 is a similar view to FIG. 1, showing the fixing of a conventional type of total hip replacement stem, FIG. 3 shows the proximal end of a femur, with three different positions of the level of resecting shown at A-A, B-B and C-C respectively, FIG. 4 is a view like FIG. 2 showing a femoral prosthesis of the invention fitted by a method if the invention to a resected femur, the prosthesis including a stem also according to the invention, and FIG. 5 is a view like FIG. 4, showing a one-piece femoral prosthesis.

To explain the present invention, reference is firstly made to FIG. 3 which shows the proximal end of a femur 15. The femur has a head 16 which is globular and forms rather more than a hemisphere. Connecting the head with the main shaft 17 of the femur is a neck 18, the transition between the head 16 and neck 18 being generally smoothly concavely curved as shown at 19. The superior border of the neck terminates at the great trochanter 20, whilst the inferior border of the neck terminates at the lesser trochanter 21.

In FIG. 3, the line A-A represents the resection level for a conventional total hip replacement, this section being taken towards the end of the neck furthest from the head 11. Line B-B represents the resection level for the prosthesis shown in EP 0579868 A2, this lying through the neck at or adjacent transition area 19 between the head and the neck of the femur.

With the present invention, as will be described, the resectioning is not carried out at a level through the neck 18, but instead is carried out through the femoral head. Accordingly the line C-C represents the resection level for one embodiment of the present invention. By resecting along the line C-C through the base of the femoral head, bone in the transition area between the femoral head and the femoral neck is retained, thus providing the opportunity for exploiting the requirements referred to in relation to FIG. 1.

Accordingly the first stage in the hip replacement method is to resect the proximal end of the femur at a level through the head 16, for example at the line C-C. By resecting the bone at this position through the base of the femoral head, it is possible then to machine the interior of the bone into the form of a truncated cone, i.e. in the form of an engine valve seating, with this frustoconical or generally frustoconical form of cavity produced thus for filling the requirements set out in relation to FIG. 1. As shown in FIG. 4, the cavity 22 is preferably symmetrical about a centre axial line E-E, and in this symmetrical form the shape of the cavity 22 facilitates milling at surgery. As will be appreciated, this machining which produces the cavity 22 is at the upper end of the medullary canal 23 which is generally curved as it extends downwardly from the neck into the main shaft 17 of the femur 15.

FIG. 4 shows an embodiment of the invention in which the femoral prosthesis is formed in two parts, namely an implant part 24 which is received in and fitted into the femur and a femoral head component 25 which is securely fitted to the implant part 24 as will be described. The implant part 24 has a curved stem part 26 which is received in and follows the shape of the medullary canal 23, the part 24 thus defining the distal end of the implant part 24. The stem part extends from a section 27 which has an external surface 28 shaped to match the internal surface of the cavity 22, i.e. the external surface of the section 28 is complementary to the frustoconical or generally frustoconical internal surface of the cavity 22 so as tightly to engage therein as shown in FIG. 4. It will be noted that the frustoconical form terminates at a free end of the section 27, in other words there is no transversely projecting collar or the like at the free end of the implant part 24 as is the case with the femoral rod shown in EP 0579868 A2. Integrally extending from the free end of the section 27 is a central outwardly tapered circular spigot 29, this spigot enabling the femoral prosthesis to be of said two-part modular type with said separate femoral head component 25 fitting onto the implant part 24 by virtue of the spigot 29 engaging in a complementarily shaped central recess 30 of the femoral head component 25. The connection between the spigot 29 and recess 30 can be frictional, or alternatively some form of adhesive cement could be used. As shown in FIG. 4, the free periphery of the femoral head component, when attached to the implant part 24, extends slightly over the resected area of the femoral bone. In an alternative embodiment, the reverse arrangement could be employed, i.e. the frustoconical spigot extends from the end of component 25 and enters a matching recess in the end of the section 27.

The prosthesis would typically be manufactured from cobalt chrome or other suitable metallic material, and the implant part 24 would generally either be cemented in place or modified for suitable biological fixation. The head component 25 could either be used as a hemi-arthroplasty with the head component articulating against the patient's normal acetabular cartilage or alternatively the head component could be articulated against a prosthetic acetabular component typically manufactured from cobalt chrome, ceramic or polyethylene material. It will thus be appreciated that with the prosthesis described and illustrated, the head component extends directly away from the section 27 received in the cavity 22 in contrast to the arrangement described and shown in EP 0579868 A2 where the head is connected via a connecting portion to the implant part so that the head is spaced from, and thus does not directly extend from the free end of the implant part which, in this prior art arrangement is constituted by the transversely projecting collar. Typically for different patients, the maximum diameter of the cavity 22, and thus effectively the maximum diameter of the section 27 received therein, is from 29 mm to 45 mm, and as shown in FIGS. 4 and 5, the cavity 22 at its maximum diameter extends across the whole, or substantially the whole of the end surface of the resected head.

Accordingly, in accordance with a method of the invention the proximal end of the femur is resected at the level of the line C-C shown in FIGS. 3 and 4, and the cavity 22 is then produced by machining, for example milling, this cavity being of frustoconical or generally frustoconical shape. As explained above, this cavity 22 is formed at the upper end of the medullary canal 23 which extends in curved fashion from the line D-D to T.

The implant part 24 is then fitted into the cavity 22 and medullary canal 23 as shown in FIG. 4 and secured therein as described above. The femoral head component 25 could already be fitted on this implant part 24 at the time of said insertion, or alternatively could be engaged onto the spigot 29 once the implant part 24 has been fitted in place. By virtue of the extent of the section 27 fitting complementarily in its machining cavity 22, the advantages of EP 0579868 are achieved in conjunction with the requirements of FIG. 1 also being satisfied to provide an improved prosthesis fixation. It will be understood that both the femoral prosthesis, including a head and an implant, either integral or separate, as well as an implant part per se are considered novel and inventive in addition to the method of fitting, including said resecting.

With regard to FIG. 5, this shows a further embodiment of a prosthesis fitted in place at the proximal end of a resected femur in a similar manner to that shown in FIG. 4. The difference here is that the prosthesis 31 is formed in one piece with the central part of its head being hollow as shown at 32. As with the embodiment shown in FIG. 4, the prosthesis would be manufactured out of cobalt chrome or similar material and the stem would be cemented in place, or modified for suitable biological fixation. Moreover as with FIG. 4, the head would, as mentioned in relation thereto, either articulate against the patient's normal acetabular cartilage or against a prosthetic acetabular component manufactured from cobalt chrome, ceramic or polyethylene material. In a similar manner to that of FIG. 5, the separate femoral head component 25 could have part thereof, for example a central part thereof, hollow.

In a further embodiment of the two-part prosthesis, the proximal end of the frustoconical aspect of section 27 could be extended to form a peripheral cone junction with the inner aspect of the femoral head component. In a still further embodiment the stem part of the one or two piece implant could be straight rather than curved.

The invention claimed is:
1. A method of fitting a femoral implant to a resected femur comprising
   resecting a femoral bone through a femoral head to provide a resected end,
   machining said resected end of the femoral bone to form a frustoconical or generally frustoconical cavity in the bone, wherein the diameter of the cavity at the resected end is substantially the same as the diameter of the surface of the resected end; and inserting into said cavity a femoral implant, which in use curves into the medullary canal of the femoral bone.

2. A method as claimed in claim 1, wherein the femoral bone is resected through the base of the femoral head.

3. A method as claimed in claim 1, wherein the cavity is symmetrical about a centre line thereof.

4. A method as claimed in claim 1, wherein at or adjacent its end the femoral implant is formed with a part having an external surface complementary to the surface of said cavity in the femoral bone so as tightly to engage therein.

5. A method as claimed in claim 4, wherein a stem part of the implant extends away from said part of the implant, and is received in said medullary canal.

6. A method as claimed in claim 5, wherein the stem part is cemented in place.

7. A method as claimed in claim 5, wherein the stem part is biologically fixed in place.

8. A method of fitting a femoral implant to a resected femur comprising the steps of:

resecting a femoral bone through a femoral head to provide a resected end;

machining said resected end of the femoral bone to form a frustoconical or generally frustoconical cavity in the bone curving into the medullary canal, said cavity is configured to receive a stem part of a femoral implant, wherein the cross sectional area of the cavity at the resected end is larger than the cross sectional area of the cavity away from the resected end and toward the medullary canal, wherein the diameter of the cavity at the resected end is substantially the same as the diameter of the surface of the resected end; and inserting into said cavity the femoral implant.

9. The method of claim 8, wherein the femoral bone is resected through the base of the femoral head.

10. The method of claim 8, wherein a portion of the cavity near the resected end is symmetrical about a centre line thereof.

11. The method of claim 8, further comprises the step of providing the femoral implant having at least a portion with an external surface complementary to the surface of said cavity in the femoral bone whereby at least said portion tightly engages the cavity.

12. The method of claim 8 further comprises the step of cementing the femoral implant to the femoral bone.

13. The method of claim 8 further comprises the step of biologically fixing the femoral implant to the femoral bone.

14. A method of fitting a femoral implant to a resected femur comprising the steps of:

resecting a femoral bone through a femoral head machining said resected end of the femoral bone to form a cavity in the bone extending into the medullary canal, said cavity configured to receive a stem part of a femoral implant wherein the cross sectional area of the cavity at the resected end is larger than the cross sectional area of the cavity away from the resected end and toward the medullary canal and wherein the diameter of the cavity at the resected end is substantially the same as the diameter of the surface of the resected end;

inserting into said cavity the femoral implant having at least a portion with an external surface complementary to the surface of said cavity in the femoral bone whereby at least said portion tightly engages the cavity; and positioning the femoral implant whereby the external surface at the periphery of a portion of a femoral head of the femoral implant is positioned against the end surface of the resected end.

15. The method of claim 14, wherein the femoral bone is resected through the base of the femoral head.

16. The method of claim 14, wherein the cavity is symmetrical about a centre line thereof.

17. The method of claim 14, wherein the cavity is configured to receive a stem part that is curved.

18. The method of claim 14 further comprises the step of cementing the femoral implant to the femoral bone.

19. The method of claim 14 further comprises the step of biologically fixing the femoral implant to the femur.

* * * * *